United States Patent [19]
Knight et al.

[11] Patent Number: 5,491,160
[45] Date of Patent: Feb. 13, 1996

[54] PESTICIDAL METHODS AND COMPOSITIONS EMPLOYING A TRIAZOLE AND A PYRETHROID

[75] Inventors: Robert J. Knight, Rainham; David P. Highwood, Sittingbourne, both of England

[73] Assignee: American Cyanamid Co., Madison, N.J.

[21] Appl. No.: 318,014

[22] Filed: Oct. 4, 1994

[30] Foreign Application Priority Data

Oct. 7, 1993 [EP] European Pat. Off. ............. 93307974

[51] Int. Cl.⁶ ........................... A01N 37/34; A01N 43/64
[52] U.S. Cl. ............................................. 514/384; 514/521
[58] Field of Search ....................................... 514/521, 384

[56] References Cited

U.S. PATENT DOCUMENTS

| | | | |
|---|---|---|---|
| 4,024,163 | 5/1977 | Elliott et al. | 260/347.4 |
| 4,210,642 | 7/1980 | Bock et al. | 424/200 |
| 4,256,754 | 3/1981 | Linhart et al. | 424/269 |
| 4,690,947 | 9/1987 | Zeck et al. | 514/521 |
| 4,742,072 | 5/1988 | Jacobson et al. | 514/384 |
| 4,783,474 | 11/1988 | Kraatz et al. | 514/383 |

FOREIGN PATENT DOCUMENTS

| | | |
|---|---|---|
| 213718 | 3/1987 | European Pat. Off. . |
| 219374A1 | 10/1983 | Germany . |

OTHER PUBLICATIONS

Worthing et al, "The Pesticide Manual", (1991) pp. 208 & 209.
Commonwealth Agricultural Bureaux Abstracts, No. 91:4376, Cab International, Farnham Royal, Slough, GB; A. Murray et al. 'RH–7988: a new selectice systemic aphicide' & Brighton Crop Protection Conference, Pest and Diseases, No. 1, 1988 pp. 73–88.
Chemical Abstracts, vol. 113, No. 9, Aug. 27, 1990, Columbus, Ohio; C. Wei et al. 'Pyrethroid Resistance in Wheat Aphids of Zhangyie' *abstract* & Kunchong Zuebao, vol. 33, No. 1, 1990, pp. 117–120.

*Primary Examiner*—Allen J. Robinson
*Attorney, Agent, or Firm*—C. F. Costello, Jr.

[57] ABSTRACT

A pesticidal composition which includes a substituted 1,2,4-triazole compound and a pyrethroid insecticide is disclosed. The pesticidal composition is particularly effective against aphid pests.

15 Claims, No Drawings

PESTICIDAL METHODS AND COMPOSITIONS EMPLOYING A TRIAZOLE AND A PYRETHROID

This invention relates to methods of combatting pests at a locus and to pesticidal compositions.

Insecticidal 1,2,4-triazole compounds are known and have been extensively described in, for example, U.S. Pat. Nos. 4 742 072, 3 308 131, 3 973 028, 4 054 664, 4 160 839, 4 220 790, European Patent Application No. 0 213 718, European Patent Application No. 0 337 815 and European Patent Application No. 0 338 685.

Insecticidal pyrethroid compounds are also well-known and have been described in, for example, U.K. Patent Application No. 1 413 491 (NRDC), European Patent Application No. 22382 (FMC), European Patent Application No. 107296 (ICI), U.K. Patent Application No. 1 565 932 (Bayer), U.K. Patent Application No. 1 439 615 (Sumitomo), U.K. Patent Application No. 1 560 303 (Sumitomo), U.K. Patent Application No. 2 013 206 (Sumitomo), and U.K. Patent Application No. 2 064 528 (Shell).

This invention is based on the discovery of a novel pesticidal method and composition which utilises both 1,2,4-triazole compounds and pyrethroid compounds.

According to a first aspect of the present invention, there is provided a pesticidal composition which includes a substituted 1,2,4-triazole compound and a pyrethroid insecticide.

Said triazole compound and said pyrethroid insecticide have, surprisingly, been found to act synergistically when used in a method of combatting pests at a locus.

Preferably, the wt. % of 1,2,4-triazole in said composition is greater than the wt. % of pyrethroid insecticide in said composition. The wt. % of 1,2,4-triazole in said composition may be at least twice, is preferably at least four times, the wt. % of pyrethroid insecticide in said composition.

Generally, when any moiety described herein comprises an alkyl group this alkyl group may be linear or branched and may suitably contain 1 to 10, preferably 1 to 6, and most preferably 1 to 4 carbon atoms, suitable examples being methyl, ethyl, propyl and t-butyl. When any groups are designated as being optionally substituted, the substituent groups which are optionally present may be any of those customarily employed in the development of pesticidal compounds, and/or the modification of such compounds to influence their structure/activity, persistence, penetration or other property. In relation to moieties which comprise an optionally substituted alkyl or alkylene group, specific examples of such substituents include halogen, especially fluorine, chlorine or bromine atoms, and nitro, cyano, hydroxyl, $C_{1-4}$ alkoxy, $C_{1-4}$ haloalkoxy, ($C_{1-4}$ alkoxy)carbonyl groups, amino and alkylamino groups; and, in relation to an alkylene group, oxo groups. It is preferred, however, that alkyl moieties are unsubstituted, or halogen-substituted and that alkylene moieties are unsubstituted, or only Substituted by alkyl. In relation to moieties which comprise an optionally substituted aryl or heteroaryl group, optional substituents include halogen, especially fluorine, chlorine and bromine atoms, and nitro, cyano, amino, hydroxyl, $C_{1-4}$ alkyl, $C_{1-4}$ haloalkyl (especially $CF_3$) and $C_{1-4}$ alkoxy groups. 1 to 3 substituents may suitably be employed. A halogen atom may most suitably be a fluorine, chlorine or bromine atom. A preferred aryl group is phenyl.

Preferably, the substituted 1,2,4-triazole compound is substituted at one position on the triazole ring by a group of general formula

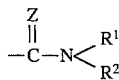

where Z is an oxygen or sulphur atom, and $R^1$ and $R^2$ independently represent a hydrogen atom, an alkyl group or together represent a chain. Preferably, Z is an oxygen atom. Preferably, $R^1$ and $R^2$ represent an alkyl group. More preferably, $R^1$ and $R^2$ represent a methyl group.

The substituted 1,2,4-triazole compound may be selected from a group of compounds having the general formula

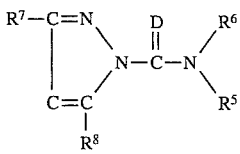

and

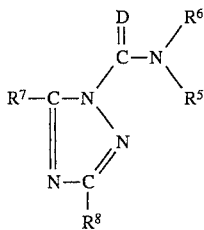

and
where D is oxygen or sulfur, $R^5$ and $R^6$ are aliphatic groups containing up to 14 carbons and which may be joined to form a heterocyclic ring with the carbamoyl nitrogen atom and $R^7$ and $R^8$, which together contain up to 14 carbon atoms, are free from aliphatic unsaturation and are selected from hydrogen, halogen, sulfonyl, mercapto, cyano, hydrocarbyl, halohydrocarbyl, nitrohydrocarbyl, hydroxycarbyloxycarbonylhydrocarbyl, hydrocarbylsulfonyl, hydrocarbylmercapto, nitrohydrocarbylmercapto, halohydrocarbylmercapto, aminohydrocarbylmercapto and hydrocarbyloxyhydrocarbyl.

The substituted 1,2,4-triazole compound may be selected from 1-N,N-dimethylcarbamoyl-3 (5)-alkyl-5 (3)-alkylthioalkylthio-1,2,4-triazoles. The 3(5) substituents may include i-propyl, s-butyl, t-butyl or optionally methyl-substituted cyclopropyl and a group having the formula

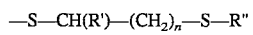

where R' is H or methyl, R" is lower ($C_1$–$C_4$)alkyl and n is zero or 1.

The substituted 1,2,4-triazole compound may be selected from 1-dimethylcarbamoyl-3-branchedalkyl-1,2,4-triazol-5-yl-(N-substituted)-sulfonamides.

The substituted 1,2,4-triazole compound may be selected from 1(2)-(N, N-disubstituted carbamoyl)-3,5-substituted-1,2,4-triazoles. The 3(5) substituents may include isopropyl, s-butyl, t-butyl, and S-R where R is methyl, ethyl, propyl, vinyl, prop-2-ynyl, but-2-enyl or 2-haloalkyl.

The substituted 1,2,4-triazole compound may be selected from 1-N,N-dimethylcarbamoyl-3,5-substituted-1,2,4-triazoles. The 3-substituents may include t-butyl, propyl, cyclopropyl, isopropyl or 1-methylpropyl. The 5-substituents may include S—$R^3$ where $R^3$ is 2-propynyl, allyl, 2-bromoallyl, 2-chloroallyl, 2-methylallyl, 1-methylallyl or 2,3,3-trichloroallyl.

The substituted 1,2,4-triazole compound may be 1-N,N-dimethylcarbamoyl -3-tert-butyl-5-methylthio-1,2,4-triazole.

Preferably, the 1,2,4-triazole compound is a 1-dimethylcarbamoyl -3-substituted-5-substituted-1H-1,2,4-triazole of general formula

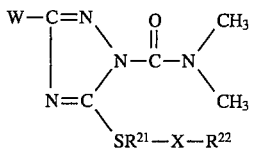   I wherein $R^{21}$ is an unsubstituted or substituted ($C_1$–$C_6$) straight chain alkylene (—($CH_2$)$_p$—) group having one to four of the same or different substituents selected from cyano; nitro; $OR^2$; $CO_2R^{23}$; $OCOR^{23}$; $COR^{23}$; ($C_2$–$C_6$)alkenyl; ($C_2$–$C_6$)alkynyl; ($C_1$–$C_6$) alkyl; or unsubstituted or substituted phenyl having one to three of the same or different halo, cyano, nitro, trifluoromethoxy, difluoromethoxy, tetrafluoroethoxy, trifluorothiomethoxy, tetrafluorothiomethoxy; $CO_2R^{23}$, $COR^{23}$, $OCOR^{23}$, ($C_1$–$C_4$)alkyl, ($C_1$–$C_4$)alkoxy, ($C_1$–$C_4$)haloalkyl or ($C_2$–$C_6$) alkenyl;

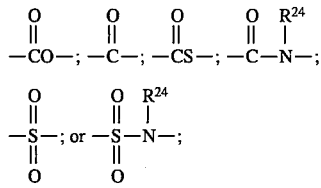

$R^{22}$ is hydrogen;
unsubstituted or substituted ($C_1$–$C_6$)alkyl where the substituent is halo, cyano, nitro, $OR^{23}$ $CO_2R^{23}$, $COR^{23}$ or $OCOR^{23}$;
unsubstituted or substituted phen($C_1$–$C_4$)-alkyl where the phenyl ring has one to three of the same or differnt substituents selected from halo, cyano, nitro, trifluoromethoxy, difluoromethoxy, tetrafluoroethoxy, trifluorothiomethoxy, tetrafluorothioethoxy, $CO_2R^{23}$, $COR^{23}$, $OCOR^{23}$, ($C_1$–$C_4$)alkyl, ($C_1$–$C_4$)alkoxy, ($C_1$–$C_4$)haloalkyl or ($C_2$–$C_6$)alkenyl;
unsubstituted or substituted phenyl having one to three of the same or different substituents selected from halo, cyano, nitro, trifluoromethoxy, difluoromethoxy, tetrafluoroethoxy, trifluorothiomethoxy, tetrafluorothioethoxy, $CO_2R^{23}$, $COR^{23}$, $COR^{23}$, $OCOR^{23}$, ($C_1$–$C_4$)alkyl, ($C_1$–$C_4$)alkoxy, ($C_1$–$C_4$)haloalkyl or ($C_2$–$C_6$)alkenyl;
$R^{24}$ is hydrogen; or ($C_1$–$C_6$) alkyl;
$R^{22}$ and $R^{24}$, together with the nitrogen atom to which they are attached, form a pyrrolidino, morpholino or piperidino ring;
W is isopropyl; sec-butyl; t-butyl; t-amyl; or 2-methylthio-2-propyl;
where R23 is hydrogen; ($C_1$–$C_6$)alkyl; or phenyl optionally substituted with one to three of the same or different halo, cyano, nitro, hydroxy, trifluoromethyl, trifluoromethoxy, difluoromethoxy, tetrafluoroethoxy, trifluorothiomethoxy, tetrafluorothioethoxy, ($C_1$–$C_4$)alkyl, ($C_1$–$C_4$)alkoxy, ($C_1$–$C_4$)haloalkyl, ($C_2$–$C_6$)alkenyl, carboxy, ($C_1$–$C_4$)alkoxycarbonyl;
and agronomically acceptable salts thereof.

Preferably in said compound of general formula I:
$R^{21}$ is an unsubstituted or substituted ($C_1$–$C_6$) straight chain alkylene group having one to four of the same or different substituents selected from $CO_2$—$R^{23}$ and ($C_1$–$C_6$) alkyl;

$R^{22}$ is hydrogen or ($C_1$–$C_6$)alkyl; and
W is t-butyl.

More preferably, in said compound of general formula I:
$R^{21}$ is —$CH_2$—, —$CH_2CH_2$—, —$CH_2CH_2CH_2$— or —CH($CH_3$)—;
X i

$R^{22}$ is hydrogen or ($C_1$–$C_4$) alkyl; and
W is t-butyl.

In the most preferred embodiment in said compound of general formula I:
$R^{21}$ represents methylene (—$CH_2$—);
X i

$R^{22}$ is an ethyl group; and
W is t-butyl.

This latter mentioned compound is known by the common name of triazamate.

Said substituted 1,2,4-triazole compounds may be prepared as described in the documents noted in the introductory part of this specification.

Examples of commercial pyrethroid insecticides for use in the pesticidal composition include: 5-benzyl-3-furylmethyl (E)-(1R)-cis-2,2-dimethyl-3-(2-oxothiolan-3-ylidenemethyl) cyclopropanecarboxylate; permethrin (3-phenoxybenzyl (1RS) -cis-trans-3 -(2,2-dichlorovinyl)-2,2-dimethylcyclopropanecarboxylate; fenpropathrin ((RS)-α-cyano-3-phenoxybenzyl 2,2,3,3-tetramethylcyclopropanecarboxylate); esfenvalerate ((S)-α-cyano-3-phenoxybenzyl (S)-2 (4-chlorophenyl) -3methylbutyrate); fenvalerate ((RS) -cyano-3phenoxybenzyl(RS)-2- (4-chlorophenyl) -3-methylbutyrate); cyfluthrin ((RS)-α-cyano-4-fluoro-3-phenoxybenzyl (1RS)-cis-trans-3-(2 , 2-dichlorovinyl) -2,2dimethylcyclopropanecarboxylate); beta-cyfluthin (a reaction mixture comprising two enantiomeric pairs in approximate ratio 1:2, i.e. (S)-α-cyano-4-fluoro-3-phenoxybenzyl (1R)-cis-3-(2,2 -dichlorovinyl)-2,2-dimethylcyclopropanecarboxylate and (R) -α-cyano-4 -fluoro-3-phenoxybenzyl (1S)-cis-3-(2,2-dichlorovinyl) -2,2-dimethylcyclopropanecarboxylate with (S)-α-cyano-4 -fluoro-3-phenoxybenzyl (1R) -trans-3-(2,2-dichlorovinyl)-2,2-dimethylcyclopropanecarboxylate and (R)-α-cyano-4-fluoro-3-phenoxybenzyl (IS)-trans-3-(2,2-dichlorovinyl)-2,2-dimethylcyclopropanecarboxylate);
lambda-cyhalothrin (a reaction product comprising equal quantities of (S)-α-cyano-3-phenoxybenzyl (Z)-(1R)-cis-3-(2-chloro-3,3,3trifluoropropenyl)-2,2-dimethylcyclopropanecarboxylate and (R)-α-cyano-3-phenoxybenzyl(Z)-(1S)-cis-3-(2-chloro-3,3,3-trifluoropropenyl) -2,2-dimethylcyclopropanecarboxylate); cyhalothrin ((RS) -α-cyano-3-phenoxybenzyl(Z)-(1RS)-cis-3-(2-chloro-3,3,3-trifluoropropenyl) -2,2-dimethylcyclopropanecarboxylate); deltamethrin ((S) -α-cyano-3-phenoxybenzyl(1R) -cis-3-(2, 2-dibromovinyl) -2,2dimethylcyclopropanecarboxylate); cypermethrin ((RS)-α-cyano-3-phenoxybenzyl (1RS) -cis-trans-3-(2,2dichlorovinyl) -1,1-dimethylcyclopropanecarboxylate); and alpha-cypermethrin (a racemate comprising (S)-α-cyano-3-phenoxybenzyl (1R)-cis-3-(2,2-dichlorovinyl )-2,2-dimethylcyclopropanecarboxylate and (R)-α-cyano-3-phenoxybenzyl (1S)-cis-3-(2,2-dichlorovinyl)-2,2-dimethylcyclopropanecarboxylate).

Preferably, said pyrethroid insecticide for use in the composition is of general formula:

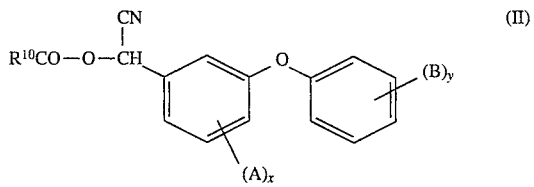

where A and B independently represent a halogen atom or a methyl group; x is 0, 1 or 2; y is 0, 1 or 2; and $R^{10}$ represents a group of general formula:

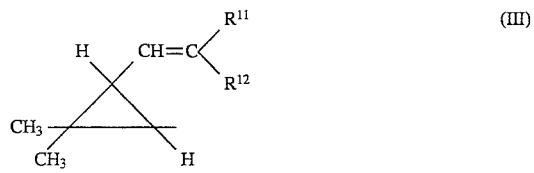

where $R^{11}$ and $R^{12}$ independently represent a hydrogen or halogen atom, or an optionally substituted $C_{1-4}$ alkyl group; or $R^{10}$ represents a group of general formula:

where $R^{13}$ represents a phenyl group optionally substituted by one or more substituents independently selected from halogen atoms, or $C_{1-4}$ alkyl, $C_{1-4}$ alkylthio, $C_{1-4}$ alkoxy, nitro and methylenedioxy groups.

Preferably, A represents a halogen atom. A preferred halogen atom is a fluorine or chlorine atom, with a fluorine atom being especially preferred.

Preferably, B represents a halogen atom. A preferred halogen atom is a fluorine or chlorine atom.

Preferably, x is 0 or 1. Where x is 1, preferably said atom or group A is substituted in the 4-position relative to the cyanomethyl group in the compound of general formula II.

Preferably, y is 0.

Where $R^{10}$ represents a group of general formula III, $R^{11}$ and $R^{12}$ may independently represent a halogen atom or an optionally substituted $C_{1-2}$ alkyl group. Preferably, $R^{11}$ and $R^{12}$ independently represent a bromine or chlorine atom or a trifluoromethyl group. Where $R^{11}$ and $R^{12}$ each represent a halogen atom, $R^{11}$ and $R^{12}$ preferably represent the same halogen atom. Where $R^{11}$ represents a trifluoromethyl group, $R^{12}$ preferably represents a chlorine atom.

Where $R^{10}$ represents a group of general formula IV, $R^{13}$ preferably represents a phenyl group optionally substituted by one or more halogen atoms. Preferred halogen atoms include fluorine and chlorine atoms. $R^{13}$ preferably represents a 4-substituted phenyl group and, more preferably, represents a phenyl group substituted by a chlorine atom. Most preferably, $R^{13}$ represents a 4-chlorophenyl group.

Preferably, said pyrethroid insecticide is alpha cypermethrin.

The pyrethroid insecticide may be prepared using known processes, for example, as described in the documents noted in the introductory part of this specification.

Said pesticidal composition preferably also includes a carrier. A carrier in the composition according to the invention is any material with which the active ingredient is formulated to facilitate application to a locus to be treated, or to facilitate storage, transport or handling. A carrier may be a solid or a liquid, including a material which is normally gaseous but which has been compressed to form a liquid, and any of the carriers normally used in formulating biocidal compositions may be used. Preferably compositions according to the invention contain 0.5 to 95% by weight of the triazole and pyrethroid.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of-sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, emulsion concentrates, suspension concentrates and aerosols. Wettable powders usually contain 25, 50 or 75% w of active ingredients and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of active ingredient. Granules are usually prepared to have a size between 10 and 100 BS mesh (1,676–0.152 mm), and may be manufactured by agglomeration or impregnation techniques. Generally, granules will contain 0.5–75% w active ingredient and 0–10% w of additives such as stabilisers, surfactants, slow release modifiers and binding agents. The so-called "dry flowable powders" consist of relatively small granules having a relatively higher concentration of active ingredients. Emulsifiable concentrates usually contain, in addition to a solvent and, when necessary, co-solvent, 10–50% w/v active ingredients, 2–20% w/v emulsifiers and 0–20% w/v of other additives such as stabilisers, penetrants and corrosion inhibitors. Emulsion concentrates are normally water-based and usually contain, in addition to a solvent and, when necessary, a co-solvent, 10–50% w/v active ingredient, 1–20% w/v emulsifiers and/or emulsion stabilisers, 0.002–20% of other additives such as antifreezes, penetrants, buffering agents, bacteriostats, corrosion inhibitors and colouring agents. Suspension concentrates are usually compounded so as to obtain a stable, non-sedimenting flowable product and usually contain 10–75% w active ingredients, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The composition of the invention may also contain other ingredients, for example other compounds possessing herbicidal, insecticidal or fungicidal properties.

The invention extends to a method of combatting pests at a locus which comprises applying to the locus a substituted 1,2,4-triazole compound and a pyrethroid insecticide.

Said substituted 1,2,4-triazole and said pyrethroid insecticide may be as described in any statement herein.

Preferably, a composition according to said first aspect is applied to said locus in said method.

Preferably, said method is a method of combatting insects at a locus. More preferably said method is a method of combatting aphid pests, for example, grain aphids (*Sitobion avenae*), at a locus.

The invention extends to the use of a ,substituted 1,2,4-triazole compound and a pyrethroid insecticide in combatting pests at a locus.

The invention further extends to the use of a composition according to said first aspect in combatting pests at a locus.

The invention will now be described further with reference to the following Examples.

In the Examples reference is made to the following

AZTEC—a Trade Name for triazamate which is ethyl (3-tert-butyl-1-dimethylcarbamoyl-1-H-1,2,4 -triazol-5-ylthio) acetate.

FASTAC is a Trade Name for alpha-cypermethrin and is particularly a racemate comprising (S) ∝-cyano-3-phenoxybenzyl(1R)-cis-3-(2,2-dichloro-vihyl )-2,2 dimethylcyclopropanecarboxylate and (R)-∝-cyano-3-phenoxybenzyl (1S) -cis-3-(2,2-dichlorovinyl)-2,2-dimethylcyclopropanecarboxylate.

The term "ai" means "active ingredient".

The term "DAT" means "days after treatment".

Example 1

Wheat seeds (*var Axona*) were planted in small plots approximately 50 cm square to give twelve "tussock" plots. Three plots were used for each of three comparative chemical treatments and three plots were used as untreated control plots. As the plants approached the "anthesis" stage, they were monitored regularly for the first signs of a developing population of grain aphid (*Sitobion avenae*). At this point the plots, which had been laid out in three blocks of four plots, were numbered sequentially and the three treatments and untreated control assigned randomly to the plots within each block.

Solutions of AZTEC and FASTAC were prepared at the concentrations required to give the dose of active ingredient stated in Table 1, when applied at a volume application rate of 400 litres/ha. The solutions were then applied to the appropriate plots using a knapsack sprayer with a single nozzle lance fitted with a cone nozzle.

Assessments of aphid populations were made by visual inspection of ten ears in each plot immediately before, and at the stated intervals after treatment. The results are provided in Table 1.

The efficacy of each treatment was calculated using the Henderson-Tilton formula:

$$\% \text{ Efficacy} = \left(1 - \frac{Ta}{Ca} \cdot \frac{Cb}{Tb}\right) \cdot 100$$

where Tb=infestation in the treated plots before application;

Ta=infestation in the treated plots after application;

Cb=infestation in the control plots before application; and

Ca=infestation in the control plots after application.

The efficacy results are provided in Table 2.

Example 2

Sixteen plots, each 3 m×10 m, were marked out in a field of growing wheat (*var Thesee*) in four blocks of four plots each. The plots were numbered sequentially and then three comparative chemical treatments and untreated controls were assigned randomly to the plots within each block.

The plots were monitored regularly for the first signs of infestation by the grain aphid, *Sitobion avenae*, and were then treated, using a pressurised knapsack precision sprayer feeding a 3 m boom fitted with flat fan nozzles, with solutions of FASTAC and AZTEC, formulated to deliver the dose of active ingredient stated in Table 3, when applied at a volume application rate of 300 litres/ha.

Assessments of aphid populations were made before, and at intervals after, treatment in both the treated and untreated control plots. Twenty-five ears were visually examined in each plot and the number of aphids thereon counted. The results are provided in Table 3.

The efficacy of each treatment was calculated using Abbott's formula:

$$\% \text{ Efficacy} = \left( \frac{Ca - Ta}{Ca} \right) \cdot 100$$

where Ca=infestation in the control plots after application; and

Ta=infestation in the treated plots after application.

The efficacy results are provided in Table 4.

The grain from each plot was harvested using a small-plot combine harvester, and the yield, corrected for moisture content, was calculated. The grain yield results are provided in Table 5.

TABLE 1

| TREATMENTS | Mean number of aphids per 10 ears | | | |
|---|---|---|---|---|
| | Pre-treatment | 2DAT | 6DAT | 10DAT |
| AZTEC (49 g ai/ha) | 14.3 | 13.0 | 17.3 | 37.3 |
| FASTAC (10 g ai/ha) | 19.0 | 2.3 | 5.7 | 27.7 |
| AZTEC/FASTAC (49/10 g ai/ha) | 56.3 | 10.0 | 17.3 | 24.7 |
| Untreated Control | 24.5 | 33.3 | 42.5 | 54.3 |

TABLE 2

| TREATMENTS | % EFFICACY | | |
|---|---|---|---|
| | 2DAT | 6DAT | 10DAT |
| AZTEC (49 g ai/ha) | 33 | 30 | 0 |
| FASTAC (10 g ai/ha) | 91 | 83 | 34 |
| AZTEC/FASTAC (49/10 g ai/ha) | 87 | 82 | 80 |

TABLE 3

| TREAT-MENTS | Mean number of aphids per ear | | | | |
|---|---|---|---|---|---|
| | Pre-treatment | 2DAT | 7DAT | 14DAT | 21DAT |
| AZTEC (70 g ai/ha) | 4.0 | 2.8 | 8.7 | 20.0 | 20.0 |
| FASTAC (10 g ai/ha) | 4.4 | 1.2 | 1.1 | 17.0 | 18.7 |
| AZTEC/ FASTAC (70/10 g ai/ha) | 5.0 | 0.7 | 1.2 | 8.3 | 10.2 |
| Untreated Control | 5.7 | 7.3 | 14.6 | 26.2 | 22.8 |

TABLE 4

| TREATMENTS | % EFFICACY | | | |
|---|---|---|---|---|
| | 2DAT | 7DAT | 14DAT | 21 DAT |
| AZTEC (70 g ai/ha) | 61 | 40 | 24 | 12 |
| FASTAC (10 g ai/ha) | 84 | 93 | 35 | 18 |
| AZTEC/FASTAC (70/10 g ai/ha) | 91 | 91 | 68 | 55 |

TABLE 5

| TREATMENTS | GRAIN YIELD (TONNES/ha) |
|---|---|
| AZTEC (70 g ai/ha) | 5.98 |
| FASTAC (10 g ai/ha) | 6.26 |
| AZTEC/FASTAC (70/10 g ai/ha) | 6.74 |

TABLE 5-continued

| TREATMENTS | GRAIN YIELD (TONNES/ha) |
|---|---|
| Untreated Control | 5.72 |

We claim:

1. A pesticidal composition which comprises synergistic effective amount of a substituted 1,2,4-triazole compound and a pyrethroid insecticide, wherein said substituted 1,2,4-triazole formula is a 1-dimethylcarbamoyl-3-substituted-5-substituted -1H-1,2,4-triazole of formula $$\begin{array}{c} W-C=N \\ | \quad\quad\quad \diagdown \\ \quad\quad\quad\quad N-C(=O)-N(CH_3)_2 \\ | \quad\quad\quad \diagup \\ N=C \\ \quad\quad SR^{21}-X-R^{22} \end{array} \quad (I)$$

wherein $R^{21}$ is $-CH_2-$, $-CH_2CH_2-$, $-CH_2CH_2CH_2-$ or $-CH(CH_3)-$; X i $$-\overset{O}{\underset{\|}{C}}O-;$$

$R^{22}$ is $(C_{1-4})$alkyl; and W is t-butyl; and agronomically acceptable salts thereof, and said pyrethroid insecticide is of formula $$R^{10}CO-O-\underset{\underset{\text{CN}}{|}}{CH}-\text{Ar}(A)_x-O-\text{Ar}(B)_y \quad (II)$$

where A and B independently represent a halogen atom; x is 0, 1 or 2, y is 0, 1 or 2; and $R^{10}$ represents a group of formula $$\begin{array}{c} H \quad\quad CH=C(R^{11})(R^{12}) \\ \diagdown\quad\diagup \\ \diagup\quad\diagdown \\ (CH_3)_2C \quad\quad H \end{array} \quad (III)$$

where $R^{11}$ and $R^{12}$ independently represent a halogen atom.

2. The composition according to claim 1, where $R^{21}$ represents methylene ($-CH_2-$); X i $$-\overset{O}{\underset{\|}{C}}O-;$$

$R^{22}$ is an ethyl group; and
W is t-butyl.

3. The composition according to claim 1 where said pyrethroid insecticide is alpha cypermethrin.

4. The composition according to claim 1 containing up to about 95 percent by weight of said substituted 1,2,4-triazole and pyrethroid insecticide.

5. A method of combatting insects at a locus which comprises applying to the locus a synergistic insecticidally effective amount of the composition of claim 1.

6. The method according to claim 5 where said insects are aphids.

7. A pesticidal composition which comprises an inert liquid or solid carrier, and synergistic effective amounts of a substituted 1,2,4-triazole compound and a pyrethroid insecticide, wherein said substituted 1,2,4-triazole compound is a 1-dimethylcarbamoyl-3-substituted-5-substituted-1H-1,2,4-triazole of formula

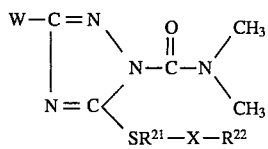 (I)

wherein $R^{21}$ is —$CH_2$—, —$CH_2CH_2$—, —$CH_2CH_2CH_2$— or —$CH(CH_3)$—;
X i

;$R^{22}$ is ($C_{1-4}$) alkyl;
and W is t-butyl; and agronomically acceptable salts thereof, and and pyrethroid insecticide is of formula

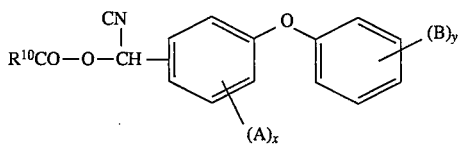 (II)

where A and B independently represent a halogen atom; x is 0, 1 or 2, y is 0, 1 or 2; and
$R^{10}$ represents a group of formula

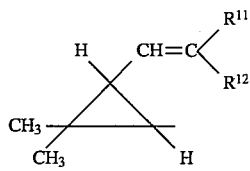 (III)

where $R^{11}$ and $R^{12}$ independently represent a halogen atom.

8. The composition according to claim 7, where $R^{21}$ represents methylene (—$CH_2$—) and $R^{22}$ is an ethyl group.

9. The composition according to claim 7 where said pyrethroid insecticide is alpha cypemethrin.

10. The composition according to claim 7 containing from about 0.5 to 95 percent by weight of said substituted 1,2,4-triazole and pyrethroid insecticide.

11. A method of combating insects at a locus which comprises applying to the locus a synergistic insecticidally effective amount of the composition of claim 7.

12. The method according to claim 11 where said insects are aphids.

13. A pesticidal composition which comprises an inert liquid or solid carrier, and synergistic effective amounts of a substituted 1,2,4-triazole compound and a pyrethroid insecticide,, wherein said substituted 1,2,4-triazole compound is a 1-dimethylcarbamoyl-3-substituted-5-substituted-1H -1,2,4-triazole of formula

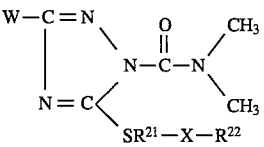 (I)

wherein $R^{21}$ is —$CH_2$—, —$CH_2CH_2$—, —$CH_2CH_2CH_2$— or —$CH(CH_3)$—;
X i

$R^{22}$ is ($C_{1-4}$) alkyl;
and W is t-butyl; and agronomically acceptable salts thereof, and
said pyrethroid insecticide is of formula

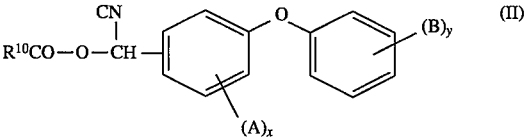 (II)

where A and B independently represent an halogen atom; x is 0, 1 or 2, y is 0, 1 or 2; and $R^{10}$ represents a group of formula

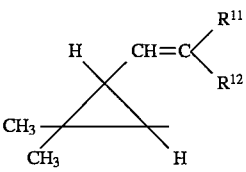 (III)

where $R^{11}$ and $R^{12}$ independently represent a halogen atom, whereby the efficacy of the pesticide composition ten days after treatment is greater than thirty five percent.

14. The composition according to claim 13, where $R^{21}$ represents methylene (—$CH_2$—) and $R^{22}$ is an ethyl group.

15. The composition according to claim 13 where said pyrethroid insecticide is alpha cypermethrin.

* * * * *

UNITED STATES PATENT AND TRADEMARK OFFICE
CERTIFICATE OF CORRECTION

PATENT NO.  :  5,491,160
DATED         :  February 13, 1996
INVENTOR(S) :  Robert Knight, et al.

It is certified that error appears in the above-identified patent and that said Letters Patent is hereby corrected as shown below:

Title page, item [73], Assignee:  should read --Shell Research Limited.--

Signed and Sealed this

Twenty-ninth Day of August, 2000

Attest:

Q. TODD DICKINSON

Attesting Officer

Director of Patents and Trademarks